United States Patent [19]

De Long

[11] 4,094,845

[45] June 13, 1978

[54] METHOD OF REDUCING LOSS OF WATER BY TRANSPIRATION AND COMPOSITION THEREFOR

[75] Inventor: Charles F. De Long, Washington, D.C.

[73] Assignee: United States Trading International, Inc., Washington, D.C.

[21] Appl. No.: 614,925

[22] Filed: Sep. 19, 1975

[51] Int. Cl.² ............... C08L 61/28; C08L 63/00; C08L 33/08

[52] U.S. Cl. ............ 260/29.4 UA; 47/DIG. 11; 260/29.3; 260/29.6 RW; 260/29.6 TA; 427/4

[58] Field of Search ........... 427/4; 71/3, 27, 29.6 NR, 71/29.6 TA, 29.6 HN, 29.6 H, 29.6 E, 29.6 AT; 47/DIG. 7, DIG. 11, 58, 29.44 A, 29.3, 29.6 RW

[56] References Cited

U.S. PATENT DOCUMENTS

| | | | |
|---|---|---|---|
| 1,931,325 | 11/1933 | Pillsbury | 47/58 |
| 3,089,280 | 5/1963 | Klaas | 47/58 |
| 3,676,102 | 7/1972 | Clark et al. | 427/4 |
| 3,682,814 | 8/1972 | Gilchrist | 204/181 |

*Primary Examiner*—Theodore E. Pertilla
*Attorney, Agent, or Firm*—Strauch, Nolan, Neale, Nies & Kurz

[57] ABSTRACT

A method for reducing loss of water from the leaves and stems of plants by transpiration and for protecting plants from damage by wind and cold consists of applying to the leaves and stems a transpiration-decreasing composition consisting essentially of an aqueous solution or dispersion of a carboxylated hydrophilic acrylic polymer, a cross-linking agent for the carboxylated hydrophilic polymer and an effective amount of an ultravioletabsorbing agent.

12 Claims, No Drawings

METHOD OF REDUCING LOSS OF WATER BY TRANSPIRATION AND COMPOSITION THEREFOR

BACKGROUND OF THE INVENTION

This invention relates to a method for reducing the loss of water from stems and leaves of plants by transpiration and protecting plants from damage by wind and cold and to a composition for this purpose.

It has long been known that most of the water applied to agricultural crops in irrigation is lost by the process of transpiration, that is, the passage of water in the form of a vapor through the plant tissue. Thus, reduction of water loss by transpiration is important both because of widespread interest in decreasing requirements for irrigation water and, in certain types of environments, for alleviating water stress. Water stress appears as a decrease in plant water potential and turgor when the transpiration rate exceeds the water supply and the transpiration capacity of the plant. When water stress occurs, plant growth reduction is observed, even when the soil is moist.

It is thought that plants benefit from transpiration by improved mineral uptake and by cooling of leaves. However, it is believed that only a very low level of transpiration is required for mineral transport. Although complete cessation of transpiration might produce an increase in leaf temperature which could result in a detrimental, or even fatal, increase in respiration/photosynthesis ratio, it is generally believed that even a relatively large decrease in transpiration, up to about 40–50% is not detrimental to plants. See, generally, A. Poljakoff-Mayber et al., "Physiological Basis and Practical Problems of Reducing Transpiration," in "Water Deficits and Plant Growth," Volume III, New York, Academic Press, Inc., (1972), following 277, and D. C. Davenport et al, "Antitranspirants - Effects and Uses in Horticulture," "The American Horticultural Magazine," Volume 50, No. 3, after 110 (Summer, 1971).

As set forth in Poljakoff-Mayber, supra, four approaches to reduction of transpiration have been tried: (1) increasing leaf reflectance so as to reduce net energy absorption; (2) using windbreaks to increase air resistance to the transfer of water vapor; (3) enclosing plants to permit humidity buildup and decrease leaf to air vapor density gradient; and (4) applying materials which tend to close the stomata of leaves or which coat the leaf surfaces so as to produce a physical barrier to diffusion and enhance the resistance of the leaves to loss of water vapor.

The application of an inert material to leaves to prevent water loss was recorded as early as 300 B.C. by Theophrastus. More recently, Miller et al, investigated the use of wax emulsions for this purpose, "Studies on the development, preparation, properties and applications of wax emulsions, for coating nursery stock and other plant materials," *Mich. Agr. Exp. Sta. Technical Bulletin* Volume 218, 1-78 (1950).

Although it had erroneously been believed that film-forming polymeric materials such as polyethylene decrease transpiration because of higher permeability to carbon dioxide and oxygen than to water vapor, it has been found that all of the materials currently in use for this purpose are, in fact, appreciably more permeable to water than to carbon dioxide. Thus, the materials generally in use hinder photosynthesis and transpiration to approximately the same extent, possibly because the materials cover only parts of the leaves. Poljakoff-Mayber, supra, at 289.

Materials which have been used to reduce loss of water by transpiration include wax emulsions, as practiced by Cushman (U.S. Pat. No. 3,847,641), liquid polyterpenes (U.S. Pat. No. 3,676,102), polymers made from isocyanates as taught by Cooke (U.S. Pat. No. 3,539,373), long chain esters of lower organic acids as suggested by Gabor (U.S. Pat. No. 3,199,944) and soluble carboxylated polymers, for example, derived from Cellosolve ® acrylate and methacrylic acid as taught by Ferguson (U.S. Pat. No. 3,157,964). Also, Klaas (U.S. Pat. No. 3,089,280) discloses the treatment of plants with an acrylic-based light-affecting composition containing optical brighteners. However, each of these compositions has one or more deficiencies. For example, the polymers used by Gabor are soluble, so that frequent applications are required to maintain effective protection against excessive transpiration. Although the main purpose of the Klaas coating is to produce a hard and brilliant finish on plants, the desired effect is achieved only by at least two coatings applied at intervals of about two to four weeks.

Polymer coatings have been applied to plants for other purposes, such as the coloring of grass. However, according to the teachings of Converse (U.S. Pat. No. 2,870,037) and Gardner (U.S. Pat. No. 2,786,821), the grasses so treated seem to have been protected from deterioration or crumbling through mechanical action of the polymer, rather than from loss of water by transpiration.

It is therefore apparent that although products are available which are essentially soluble and which are easily applied, such products are also washed from the sprayed plants following an unpredictable time interval based primarily on the frequency of rainfall. Thus, known compositions must be reapplied frequently to maintain their efficacy. Furthermore, most of the known products have varying stability to ultraviolet radiation in sunlight, so that the products deteriorate and then wash away. There is at present no product applied to the leaves and stems of plants which has an active applied life exceeding much more than about three weeks.

Therefore, there is a continuing need for transpiration-reducing and plant protecting compositions which are easily applied and have long-term efficacy and stability.

SUMMARY OF THE INVENTION

It has been found, in accordance with this invention, that leaves and stems of plants can be protected over the long term against water loss by transpiration as well as from damage by wind and cold by application to the leaves and stems of a transpiration-decreasing composition consisting essentially of an aqueous solution or dispersion of a carboxylated hydrophilic acrylic polymer, a cross-linking agent for the carboxylated hydrophilic polymer and an effective amount of an ultraviolet-absorbing agent.

As used in the specification and claims, "carboxylated hydrophilic acrylic polymer" means any copolymer which contains at least some carboxylic acid groups introduced by polymerization of an alpha,beta-unsaturated acid. Examples of alpha,beta-unsaturated acids for the purposes of this invention include acrylic acid, methacrylic acid, itaconic acid, crotonic acid, maleic acid, citraconic acid, ethacrylic acid and the like. Acrylic acid is preferred.

Monomers usable in the preparation of the carboxylated hydrophilic polymers of this invention include the lower alkyl acrylate and methacrylate esters and monomers polymerizable therewith, including, but not limited to, styrene, vinyl acetate, ethyl vinyl ether, substituted styrenes, and the like. However, the hydrophilic carboxylated polymers prepared from lower alkyl acrylates and methacrylates and carboxylic monomer exclusively are preferred. Typical of the esters preferred for making the carboxylated hydrophilic copolymers are the $C_1$-$C_4$ alkyl acrylates and methacrylates, such as methyl acrylate, ethyl acrylate, n-propyl acrylate, isopropyl acrylate, the butyl acrylates and the corresponding methacrylates. Especially preferred monomers are methyl methacrylate, ethyl methacrylate, butyl acrylate, ethyl acrylate, methyl acrylate and mixtures thereof, particularly with from about 5% to about 20% by weight of acrylic acid monomer.

A composition particularly preferred for the purposes of this invention consists of a copolymer based on about 56% by weight of methyl methacrylate, about 30% by weight of ethyl methaacrylate and about 14% by weight of acrylic acid. An equally preferred composition is based on about 44% by weight of butyl acrylate, 40% by weight of methyl acrylate and about 16% by weight of acrylic acid. Also preferred is a polymer containing about 90% by weight of ethyl acrylate and about 10% by weight of acrylic acid units.

Typical of commercially available hydrophilic polymers which can be used according to this invention is Carboset ®514H, a dispersion in ammonia water (40% solids) or solution in isopropanol (70% solids) available from the B. F. Goodrich Chemical Co. Carboset 514H ® is a dispersion of an all-acrylic resin in which polar functionality is supplied by carboxyl groups. The polymer has a molecular weight of 30,000 and an acid number of 60-70.

For ease of application, the copolymer or terpolymer is preferably solubilized in water by adjustment of the pH to 8 or higher. Suitable materials for adjustment of the pH include sodium hydroxide, ammonium hydroxide, potassium hydroxide or organic amines, including but not limited to dimethylamine, diisopropylamine, morpholine, triethylamine, ethylenediamine, 2-methylpiperazine, monoamylamine, dibutylamine, 2-amino-2-methyl-1,3-propanediol, and the like. Of the foregoing, ammonium hydroxide and diisopropylamine are preferred. It is thought that the amines vaporize during the curing process.

The molecular weight of the copolymer or terpolymer prior to cross-linking can vary between about 5000 and three million. Preferably, the molecular weight is between about 10,000 and 100,000. Although it is difficult to determine the molecular weight of the product after cross-linking, it is thought generally to be up to one million or higher.

Cross-linking agents suitable for the purposes of this invention include difunctional and polyfunctional materials which react with the carboxyl groups of the hydrophilic acrylic polymers used herein. Exemplary of cross-linking agents which convert the hydrophilic polymers of this invention to essentially permanent transpiration-decreasing compositions are formaldehyde-condensation resins, epoxy compounds and multivalent metal ions. Formaldehyde resins include those based on melamine, such as the methylol melamines and the lower molecular weight melamine-formaldehyde resins as well as methylolated phenols and lower molecular weight phenol-formaldehyde resins. Epoxy compounds include diglycidyl and triglycidyl ethers and low molecular weight epoxy resins. Typical of multivalent metal ions which can be used are zinc, chromium, aluminum, iron, calcium and titanium, in the form of salts, oxides or hydroxides.

Among commercially available formaldehyde resins which can be used as cross-linking agents are melamine-formaldehyde resins such as Resimene ® RF 5306 (Monsanto Chemical Co.) and Cyme ® 300 (American Cyanamid Co.). Melamine-formaldehyde resins and methylolated melamine derivatives are among the cross-linking agents preferred for the practice of this invention.

Commercially available epoxy compounds for the purposes of this invention include Epon ® 828 (Shell Chemical Co.), the digylcidyl ether derived from epichlorohydrin and bisphenol A; Epon ® 812 (Shell Chemical Co.), the triglycidyl ether of glycerol; Eponite ® 100 (Shell Chemical Co.), a water-dispersible epoxy resin; and DER 332 (Dow Chemical Co.). Preferred epoxy compounds are the diglycidyl and triglycidyl ethers, especially bisphenol A diglycidyl ether and glycerine triglycidyl ether.

Although a variety of metallic ions can be used to provide cross-linking, the preferred system is one in which the cross-linking agent is zinc ions. A convenient way of preparing materials using zinc ions as cross-linking agent is to use a solution of zinc ammonium carbonate complex, which is added to the solution or dispersion of polymer.

The amount of cross-linking agent can be varied from about 1% to about 20% by weight (as solids) of hydrophilic acrylic polymer. Preferably the amount of cross-linking agent is from about 1% to about 5% by weight of the hydrophilic acrylic resin.

Although the compositions prepared according to this invention ultimately become cross-linked and permanently adhere to the plants being protected against transpiration, it will be understood that the compositions used according to this invention have a reasonable life. Thus, a system consisting of a carboxylated acrylic terpolymer and a glycidyl ether has a life of about six days at room temperature, so that compositions for the practice of this invention can be prepared several days before use. Compositions using melamine-formaldehyde resins as the cross-linking agent have an apparently indefinite shelf life. Preferably, however, the hydrophilic acrylic resin and cross-linking agent are mixed just prior to use so that the products are of low viscosity for ease of application.

"Ultraviolet-absorbing agent," as used in the specification and claims, means a material which is compatible with the carboxylated hydrophilic acrylic polymer and cross-linking agent and which absorbs incident radiation in the range between about 2700 A and about 4000 A. Amoung materials known to function as ultraviolet-absorbing agents are coumarin ethers; esters of paraaminobenzoic acid, such as the glyceryl ester; esters of substituted para-aminobenzoic acids and para-methoxycinnamic acid, e.g., the 2-ethoxyethyl ester; benzophenone derivatives, e.g., 2-hydroxy-4-methoxybenzophenone; triazolylketones, such as 2-phenyl-4-(2',4'-dihydroxybenzoyl)-v-triazoles and the corresponding ethers and esters; hydrazones derived from aromatic aldehydes; 2-phenylbenzoxazole derivatives;

bisoxalic acid diamides; benzoylbenzofuran derivatives; fromazan derivatives and metal chelates of bicyclononanedione esters; bis-alpha-cyano-beta,beta-diphenylacrylic acid derivatives; 2-aryl-4,5-arylo-1,2,3-triazoles; beta-benzoyloxy-2'-hydroxychalcones; and the like.

The preferred ultraviolet-absorbing materials used in accordance with this invention are those which absorb from about 2700 A to about 3300 A. Among compounds which absorb selectively in this more limited region are benzoylbenzofurans (Baron et al., U.S. Pat. No. 3,448,190), which absorb primarily from about 2900 A to about 3200 A and various cinnamate esters, which absorb from about 2700 A to about 3300 A. Particularly preferred as an ultraviolet-absorber is 2-ethoxyethyl p-methoxycinnamate, available under the trade name of Giv-Tan ® F from Sindar Division of Giuvadan Corp., Clifton, N.J.

The amount of ultraviolet-absorbing agent can be as little as about 0.0001% by weight of the solution or dispersion of this invention. Although it is possible to use amounts as high as about 1% by weight of ultraviolet-absorbing agent, the preferred range of ultraviolet-absorbing agent is from about 0.0005% to about 0.30% by weight of the solution or dispersion.

The solutions or dispersions of this invention can contain as low as 3% by weight of solids, in the form of carboxylated hydrophilic acrylic polymer and cross-linking agent, up to a maximum of about 30% by weight. However, the preferred level of solids is from about 5% to about 15% by weight of the dispersion.

Herbicides, fungicides, insecticides or nematocides are optional additives to the compositions of this invention. Thus, in addition to protecting agricultural crops against excessive loss of water by transpiration, the compositions of this invention can be used as carriers for these agents, which are thought to leach slowly from the compositions and which are therefore administered to the crops over a prolonged period of time.

Illustrative of herbicides, fungicides, insecticides and nematocides which can be added to the compositions of this invention are copper carbonate, copper oleate, methyl-1-(butylcarbamoyl)-2-benzimidazole carbamate, 2,6-dichloro-4-nitroaniline, coordination product of zinc and manganese ethylene bisdithiocarbamate (Dithane M-45), 1-chloro-2-nitropropane, 8-hydroxyquinoline sulfate, triphenyltin hydroxide, 0,0,0',0'-tetramethyl-0,0'-dithiodi-p-phenylene phosphorothioate, 0-[2-chloro-1-(2,5-dichlorophenyl)-vinyl]-0,0-diethyl phosphorothioate, aldrin, allethrin, 2-isopropoxyphenyl N-methyl carbamate, benzene hexachloride (BHC), chlordane, ethyl 4,4'-dichorobenzanilate, 1,1-dichloro-2,2bis(p-chlorophenyl)-ethane, 1,1,1-trichloro-2,2-bis(p-chlorophenyl)ethane (DDT), 0,0-dimethyl-0-(2,2-dichlorovinyl)phosphate (DDVP), Dieldrin, tetramethyl phosphorodiamidic fluoride, 2-sec-butyl-4,6-dinitrophenyl isopropyl carbonate, Endrin, 0,0,0',0'-tetraethyl-S,S'-methylene biphosphorodithioate, heptachlor, dibasic lead arsenate, 0,0'-diethyl-0-p-nitrophenyl phosphorothioate (Parathion), piperonyl butoxide, p-chlorophenyl phenyl sulfone, 2(ethylamino)-4-(isopropylamino)-6-(methylthio)-s-triazine, N,N'-diallyl-2-chloroacetamide, 2,4-dichlorophenoxyacetic acids and its salts (2,4-D derivatives), diphenylacetonitrile, 3-phenyl-1,1-dimethylurea, 3-phenyl-1,1-dimethylurea trichloroacetate, 3-(p-chlorophenyl)-1,1-dimethylurea, 1-naphthyl N-methylcarbamate (Sevin), pentachlorophenol, trichloronitromethane (chloropicrin), 1,2-dibromo-3-chloropropane and the like.

The amount of herbicide, fungicide, insecticide or nematocide added to the compositions of this invention is generally from about 0.005% to about 1% by weight of the total of hydrophilic acrylic resin and cross-linking agent, preferably from about 0.05% to about 0.07% by weight.

The method of this invention contemplates application to the leaves and stems of plants by any of a variety of conventional techniques, including but not limited to moist spraying and pressure spraying. Generally, the amount of composition applied is from about five gallons to about fifty gallons of dispersion or solution, including the ultraviolet absorber and any other desired additives, per acre. Preferably, the level of application is at a rate of five gallons per acre.

The following examples depict in more detail the preparation of representative compositions and methods of their application in accord with the principles of the present invention.

EXAMPLE 1

A transpiration-decreasing composition was made by charging the following into a 55-gallon reactor equipped with a propeller agitator and stirring vigorously until a homogeneous dispersion was obtained:

| | |
|---|---|
| water | 120 liters |
| terpolymer (56% by weight of methyl methacrylate, 30% ethyl methacrylate, 14% of acrylic acid; molecular weight 30,000; 30% solids in water; pH 7.5; | 30 liters |
| glycerol triglycidyl ether | 3 liters |
| 2-ethoxyethyl p-methoxycinnamate | 80 milliliters |

The dispersion obtained was sprayed on an ornamental pepper plant, which, along with a control, was treated under freezing conditions (15° F for six hours). The treated plant was unaffected, whereas the leaves in the control plant drooped after exposure and the fruit appeared damaged.

Similar results were obtained with other representative flowers, trees and shrubs, which in each case were protected from moisture loss as well as from the wind and cold. Trials with agricultural crops at the University of Delaware Agricultural Station were equally successful.

EXAMPLE 2

The diglycidyl ether obtained by reaction between epichlorohydrin and bisphenol A (Epon ® 828, Shell Chemical Co.) was substituted for Epon ® 812 used in Example 1. The resulting dispersion was sprayed on flowers, trees and shrubs with the same results as in Example 1.

EXAMPLE 3

Sevin ® (1-naphthyl N-methylcarbamate, two pounds) was added to 100 gallons of composition prepared according to Example 1. The combination was sprayed on maple trees. Damage by gypsy moths was markedly decreased, compared to unsprayed trees, for a period of one year following the spraying.

EXAMPLE 4

Weed killer (2,4-D, 2,4-dichlorophenoxyacetic acid, two pounds) was added to 100 gallons of composition prepared according to Example 1. The solution was sprayed on weeds commonly found in gardens. The weeds were destroyed by one application.

EXAMPLE 5

Liquid fertilizer (12-6-6, N-P-K; one gallon) was added to 100 gallons of solution prepared according to Example 1. The mixture was sprayed on trees and shrubs. Growth was markedly improved.

EXAMPLE 6

A transpiration-decreasing composition was prepared by mixing the following materials in a ten-gallon stainless steel can equipped with mechanical stirring:

| | |
|---|---|
| water | 6 gallons |
| terpolymer (56% by weight of methyl methacrylate, 30% of ethyl methacrylate, and 14% of acrylic acid; molecular weight 30,000; 30% solids in water) | 3 gallons |
| cross-linking agent (Epon ® 812) | 0.3 gallon |
| 2-ethoxyethyl p-methoxycinnamate | 4 ounces |

The resultant solution (pH 7.5) was sprayed on potted roses. Retention of water and increase in number and size of blooms was observed.

EXAMPLE 7

An aqueous dispersion is prepared from:

| | |
|---|---|
| copolymer (90% by weight of ethyl acrylate and 10% of acrylic acid; 30% solids by weight in aqueous ammonia solution; pH 7.5; | 30 liters |
| ammonia solution (3% by weight of ammonia) | 45 liters |
| polyethylenimine (molecular weight 40,000-60,000; 40% solution in water) | |
| glycerine triglycidyl ether | 3 liters |
| 2-ethoxyethyl p-methoxycinnamate | 3 liters |

The ingredients of the dispersion are combined. The concentrate so obtained is diluted with seven parts by volume of water before spraying on plants. Results are similar to those obtained according to Examples 1 and 2.

EXAMPLE 8

An aqueous dispersion is prepared from:

| | parts by weight |
|---|---|
| terpolymer (44% by weight of butyl acrylate, 40% of methyl acrylate and 16% of acrylic acid; 30% solids in ammonia water; pH 7.5; molecular weight 16,000) | 40 |
| zinc ammonium carbonate complex | 2 |
| 2-ethoxyethyl p-methoxycinnamate | 24 |
| ammonium hydroxide solution (3% by weight of ammonia) | 90 |
| polyethylenimine (molecular weight 30,000-40,000; 40% solution in water) | 200 |
| deionized water | 300 |

The zinc ammonium carbonate complex is prepared by dissolving 7.2 parts by weight of ZnO and 21.7 parts of ammonium carbonate in 71.4 parts by weight of water and then adding 8.7 parts by weight of concentrated ammonium hydroxide.

The zinc cross-linked polymer thus obtained is applied according to the preceding examples. Results are comparable.

EXAMPLE 9

A mixture of 375 parts by weight of Carboset$^R$ 514H (40% solids in ammonia water), 542 parts of demineralized water, 83 parts of Resimene ® RF 5306 (melamine-formaldehyde resin; Monsanto Chemical Co.) and 25 parts of 2-ethoxyethyl p-methoxycinnamate is prepared by combining the Carboset ® 514H and water and then adding the Resimene ® RF 5306 slowly along with the Giv-Tan ® and stirring until the mixture is uniform. The product is sprayed on plants, with results being similar to those obtained according to the foregoing examples.

It will be appreciated that the instant specification and foregoing examples are set forth by way of illustration and not limitation and that various modifications and changes may be made without departing from the spirit and scope of the present invention, which is intended to be limited only by the appended claims.

What is claimed is:

1. Composition for decreasing the loss of water from leaves and stems of plants by transpiration and for protecting plants from damage by wind and cold consisting essentially of an aqueous solution or dispersion of a carboxylated hydrophilic acrylic polymer, a cross-linking agent for the carboxylated hydrophilic acrylic polymer and an effective amount of an ultraviolet-absorbing agent, wherein the carboxylated hydrophilic acrylic polymer and the cross-linking agent together comprise from about 3% to about 30% by weight of the aqueous solution or dispersion, said carboxylated hydrophilic acrylic polymer is a copolymer containing monomer units from at least one $C_1$-$C_4$ alkyl acrylate or methacrylate and from about 5% to about 20% by weight of at least one carboxylic monomer, and the amount of cross-linking agent is about 1% to about 20% by weight of solids of said carboxylated hydrophilic acrylic polymer.

2. The composition of claim 1, wherein the effective amount of the ultraviolet-absorbing agent is from about 0.0005% to about 0.30% by weight of the aqueous solution of dispersion.

3. The composition of claim 1, wherein the ultraviolet-absorbing agent absorbs from about 2700 A to about 3300 A.

4. The composition of claim 1, wherein the carboxylated hydrophilic acrylic polymer is a copolymer containing monomer units from at least one $C_1$-$C_4$ alkyl acrylate or methacrylate and from about 5% to about 20% by weight of acrylic acid monomer.

5. The composition of claim 1, wherein the cross-linking agent is selected from the group consisting of diglycidyl and triglycidyl ethers and low molecular weight epoxy resins.

6. The composition of claim 1, wherein the cross-linking agent is selected from the group consisting of methylolated melamines and low molecular weight melamine-formaldehyde resins.

7. The composition of claim 1, wherein the cross-linking agent is a multivalent inorganic salt, oxide or hydroxide.

8. The composition of claim 1, wherein the cross-linking agent is selected from zinc oxide, zinc carbonate and ammoniacal complexes thereof.

9. The composition of claim 1, wherein said composition also contains an effective amount of at least one herbicide, fungicide, insecticide or nematocide.

10. The composition of claim 1, wherein the carboxylated hydrophilic acrylic polymer contains monomer units from about 56% by weight of methyl methacrylate, about 30% by weight of ethyl methacrylate and about 14% by weight of acrylic acid, wherein the crosslinking agent is a diglycidyl or trigylcidyl ether and wherein the ultraviolet-absorbing agent is 2-ethoxyethyl p-methoxy-cinnamate.

11. The composition of claim 1, wherein said carboxylated hydrophilic acrylic copolymer contains monomer units from about 44% by weight of butyl acrylate, 40% by weight of methyl acrylate and about 16% by weight of acrylic acid.

12. The composition of claim 1, wherein said carboxylated hydrophilic copolymer contains monomer units from about 90% by weight of methyl acrylate and about 10% by weight of acrylic acid.

* * * * *

UNITED STATES PATENT OFFICE
CERTIFICATE OF CORRECTION

Patent No. 4,094,845        Dated June 13, 1978

Inventor(s) Charles F. De Long

It is certified that error appears in the above-identified patent and that said Letters Patent are hereby corrected as shown below:

In the Abstract, last line, separate (2 words) --ultraviolet absorbing--.

Column 4, line 59, correct spelling of --Among--.

Column 6, line 10, change "moist" to --mist--.

Column 8, line 41 (claim 2), change "of" to --or--.

Signed and Sealed this

Fourteenth Day of November 1978

[SEAL]

Attest:

RUTH C. MASON
Attesting Officer

DONALD W. BANNER
Commissioner of Patents and Trademarks